United States Patent [19]

Tessier et al.

[11] Patent Number: 4,849,443
[45] Date of Patent: Jul. 18, 1989

[54] INDOLES AND PESTICIDAL USE THEREOF

[75] Inventors: Jean Tessier, Vincennes; Jacques Demassey, Montevrain; Jean-Pierre Demoute, Montreuil-sous-Bois, all of France

[73] Assignee: Roussel Uclaf, Paris, France

[21] Appl. No.: 96,849

[22] Filed: Sep. 14, 1987

[30] Foreign Application Priority Data

Sep. 18, 1986 [FR] France ................... 86 13051

[51] Int. Cl.$^4$ ............... C01D 209/18; C01D 209/22; C01D 209/24; A01N 43/38
[52] U.S. Cl. .................... 514/419; 548/494; 548/505; 548/508
[58] Field of Search ............ 548/505, 494, 508; 514/419

[56] References Cited

U.S. PATENT DOCUMENTS 4,737,513  4/1988  Tessier et al. .

FOREIGN PATENT DOCUMENTS 0176387  4/1986  European Pat. Off. .
0261035  3/1988  European Pat. Off. ............ 548/505
2218316  9/1974  France .

Primary Examiner—David B. Springer
Attorney, Agent, or Firm—Bierman and Muserlian

[57] ABSTRACT

A compound of the formula

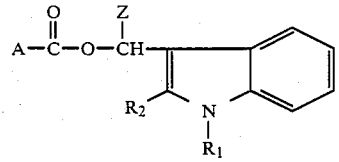

wherein A is the residue of a ACOOH pyrethrinoid acid, Z is selected from the group consisting of hydrogen, —CN, —C≡CH, —CH$_3$ and alkyl of 1 to 3 carbon atoms, R$_1$ is selected from the group consisting of hydrogen, alkyl of 1 to 8 carbon atoms, alkenyl and alkynyl of 2 to 8 carbon atoms, cycloalkyl, cycloalkenyl and cycloalkynyl of 3 to 8 carbon atoms, aryl of 6 to 14 carbon atoms and aralkyl of 7 to 18 carbon atoms and R$_2$ is selected from the group consisting of hydrogen, halogen, alkyl of 1 to 8 carbon atoms, alkenyl and alkynyl of 2 to 8 carbon atoms, cycloalkyl, cycloalkenyl and cycloalkynyl of 3 to 8 carbon atoms, aryl of 6 to 14 carbon atoms, aralkyl of 7 to 18 carbon atoms, —CN, —CF$_3$, —NO$_2$ and —COOAlK and AlK is alkyl of 1 to 18 carbon atoms having pesticidal activities.

17 Claims, No Drawings

INDOLES AND PESTICIDAL USE THEREOF

STATE OF THE ART

U.S. Pat. No. 4,380,656, No. 4,418,202, No. 4,458,090, No. 4,212,879 and No. 4,229,352 relate to pyrethrinoid esters with a different alcohol moiety.

OBJECTS OF THE INVENTION

It is an object of the invention to provide the novel alcohols of formula II and the esters of formula I and their preparation.

It is another object of the invention to provide novel pesticidal compositions and a novel method of combatting pests.

These and other objects and advantages of the invention will become obvious from the following detailed description.

THE INVENTION

The novel compounds of the invention are a compound of the formula

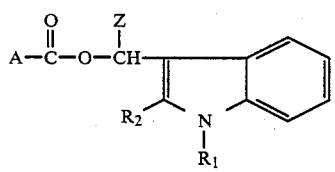

I wherein A is the residue of a ACOOH pyrethrinoid acid, Z is selected from the group consisting of hydrogen, —CN, —C≡CH, —CF$_3$ and alkyl of 1 to 3 carbon atoms, R$_1$ is selected from the group consisting of hydrogen, alkyl of 1 to 8 carbon atoms, alkenyl and alkynyl of 2 to 8 carbon atoms, cycloalkyl, cycloalkenyl and cycloalkynyl of 3 to 8 carbon atoms, aryl of 6 to 14 carbon atoms and aralkyl of 7 to 18 carbon atoms and R$_2$ is selected from the group consisting of hydrogen, halogen, alkyl of 1 to 8 carbon atoms, alkenyl and alkynyl of 2 to 8 carbon atoms, cycloalkyl, cycloalkenyl and cycloalkynyl of 3 to 8 carbon atoms, aralkyl of 7 to 18 carbon atoms, —CN, —CF$_3$, —NO$_2$ and —COOAlk and Alk is alkyl of 1 to 18 carbon atoms.

When Z is alkyl, it is preferably methyl and when R$_1$ or R$_2$ are alkyl, it is preferably methyl, ethyl, propyl or linear or branched butyl, pentyl, hexyl, heptyl or octyl. When R$_1$ or R$_2$ are alkenyl or alkynyl, they are preferably allyl, 1-propenyl, 2-propenyl or 1-(2-propynyl). Examples of R$_1$ and R$_2$ as cycloalkyl are cyclopropyl, cyclobutyl, cyclopentyl or cyclohexyl. Examples of R$_1$ and R$_2$ as aryl or aralkyl are phenyl, naphthyl, benzyl, phenethyl, phenylpropyl, phenylbutyl, phenylpentyl or phenylhexyl.

Among the preferred compounds of formula I are those wherein R$_2$ is —CF$_3$ and those wherein R$_1$ is —CH$_2$—C≡CH, hydrogen or benzyl. Other preferred compounds are those wherein A is selected from the group consisting of

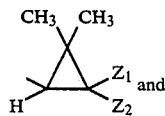

and

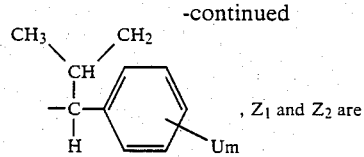

$Z_1$ and $Z_2$ are methyl or $Z_1$ is hydrogen and $Z_2$ is selected from the group consisting of

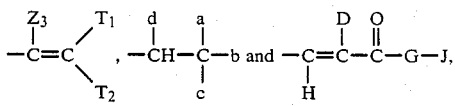

$Z_3$ is hydrogen or halogen, $T_1$ and $T_2$ are individually selected from the group consisting of hydrogen, halogen, alkoxy and alkyl of 1 to 8 carbon atoms, —CF$_3$, —CN and phenyl optionally substituted with halogen or $T_1$ and $T_2$ taken with the carbon atoms form cycloalkyl of 3 to 6 carbon atoms or

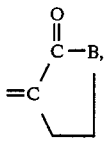

B is —O— or —S—, a,b,c and d are individually halogen, D is selected from the group consisting of hydrogen, halogen and alkoxy of 1 to 8 carbon atoms, G is —O— or —S—, J is selected from the group consisting of alkyl of 1 to 8 carbon atoms, alkenyl and alkynyl of 2 to 8 carbon atoms, cycloalkyl, cycloalkenyl and cycloalknynyl of 3 to 8 carbon atoms, aryl of 6 to 14 carbon atoms and heterocycle, all optionally substituted with at least one functional group, U is in any position of the ring and is selected from the group consisting of halogen and alkyl and alkoxy of 1 to 8 carbon atoms, m is 0,1 or 2 and when 2', the U's may be different.

More preferred compounds are those wherein A is

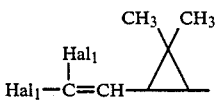

and Hal$_1$ is halogen, those wherein A is

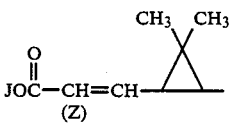

(Z)

and J is selected from the group consisting of alkyl of 1 to 8 carbon atoms and cycloalkyl of 3 to 8 carbon atoms, both optionally substituted with at least one halogen Hal$_2$ and the double bond has Z geometry and those wherein A is

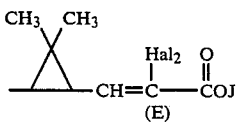

(E)

wherein Hal₂ is halogen and J is alkyl of 1 to 8 carbon atoms or cycloalkyl of 3 to 8 carbon atoms and the double bond has E geometry. Hal₂ is preferably fluorine.

The most preferred compound of the invention is [1-(2-propynyl)-2-trifluoromethyl-(1H)-indol-3-yl]-methyl 1R, cis(ΔZ) 2,2-dimethyl-3-[(1,1,1,3,3,3-hexafluoro-2-propyloxy)-3-oxo-1-propenyl]-cyclopropane carboxylate.

The novel process of the invention for the preparation of the compounds of formula I comprises reacting an alcohol of the formula

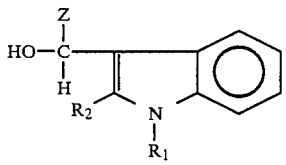

wherein Z, $R_1$ and $R_2$ have the above definitions with an acid of the formula

A COOH    III or a functional derivative thereof where A has the above definition to form the corresponding compound of formula I. Preferably, the reaction is effected in the presence of dicyclohexylcarbodiimide and 4-dimethylamino-pyridine.

The compounds of formula II are novel and may be prepared from indole or the corresponding substituted indoles as indicated in the examples. Preferred are [2-trifluoromethyl-(1H)-indol-3-yl]-methanol, [1-benzyl-2-trifluoromethyl-(1H)-indol-3-yl]-methanol, [1-(2-propynyl)-2-trifluoromethyl-(1H)-indol-3-yl]-methanol, 1(RS) [1-(2-propynyl)-2-trifluoromethyl-(1H)-indol-3-yl]-ethanol and 1(RS) [1-(2-propynyl)-2-trifluoromethyl-(1H)-indol-3-yl]-prop-2-ynyl alcohol.

The compounds of formula III are the pyrethrinoid acids used to form biologically active pyrethrinoid esters.

The novel pesticidal compositions of the invention are comprised of a pesticidally effective amount of at least one compound of formula I and an inert carrier. The compositions are useful to combat pests such as parasites of vegetables and of warm-blooded animals such as cattle, sheep and fowl as well as parasites of premises and are particularly useful to combat insects, nematodes and parasitic acariens which attack warm-blooded animals and vegetables.

The compositions of the invention are particularly useful to combact insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles. The insecticidal compositions of the invention are particularly preferred and may contain 0.005 to 10% by weight of the active ingredient.

In the advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premise use may be prepared as a spraying oil containing the active ingredient and the oil may soak the wick of a lamp which is then subjected to combustion. The concentration of the compound of formula I in the oil is preferably 0.03 to 95% by weight.

The compositions of the invention are also useful to combat acariens and nematode parasites of vegetables containing at least one compound of formula I as the active ingredient and they may be in the form of powders, granules, suspensions, emulsions or solutions.

For acaricide use, the compositions are preferably wettable powders for foliar spraying containing 1 to 80% of the active ingredient or liquids for foliar spraying containing 1 to 500 g/l of the active ingredient. Also useful are powders for foliar powder containing 0.05 to 3% by weight of the active ingredients. For nematocide use, the compositions are in the form of liquids for soil treatment containing 300 to 500 g/l of the active ingredient. For acaricide and nematocide, use, the preferred dose of the active compounds is 1 to 100 g per hectare.

The compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substance in the mixture. The vehicle used may be a liquid such as water, alcohol, hydrocarbons or other organic solvents or a mineral, animal or vegetable oil or a powder such as talc, clays, silicates or Kieselguhr or a combustible solid.

The compositions of the invention are also useful to combat acarien parasites of warm-blooded animals such as ticks, especially ticks of Boophilus species, Hyalomnia species, Amblyomnia species and Rhipicephalus species and to combat all sorts of scabies such as scarcoptic scabies, psoroptic scabies and chlorioptic scabies. They can also be useful to combat lice and helminthes. The invention also includes compositions intended to combat parasites of warm-blooded animals, especially ticks and gales, containing at least one compound of formula I.

The said compounds may be administered externally by vaporization, by shampooing, by painting or by bathing. For veterinary usage, the compositions may also be administered by painting the dorsal spine by the "pour on" method. When the "pour on" method is used, it is preferred to use solutions containing from 0.5 to 5 g of active material per 100 ml of solution.

When the compositions are to be used to .bat parasitic acariens of animals, the active compou..ds of formula I are very often incorporated into alimentary compositions in association with a nutritive mixture adapted to the animal to be fed. The nutritive mixture will vary depending upon the species of animal but usually contains cereals, sugars and grains, soybean press cake, peanuts and turnsole press cakes, meal of animal origin such as fish meal, synthetic amino acids, mineral salts, vitamins and antioxidants.

Another feature of the invention are insecticidal, acaricidal or nematocidal compositions containing as an active ingredient at least one compound of formula I and as a second active ingredient at least one pyrethrinoid ester selected from the group consisting of esters of allethrolone, of 3,4,5,6-tetrahydrophthalimido-methyl alcohols, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimido-methyl alcohol, 5-benzyl-3-furyl-methyl alcohols, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisiomer forms.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-hepthyl)-bicyclo-[2,2-1]-5-heptene-2,3-dicarboximide or piperonyl-bis-2-(2'-n-butoxy-ethoxy)-ethyl acetal (tropital).

The novel method of the invention for combatting parasites such as insects, nematodes and acariens comprises contacting the parasites with a pesticidally effective amount of at least one compound of formula I In the following examples there are described several preferred embodiments to illustrate the invention. However, it should be understood that the invention is not intended to be limited to the specific embodiments.

EXAMPLE 1

[2-trifluoromethyl-(1H)-indol-3-yl]-methyl 1R, cis 3-(2,2-dibromoethenyl)-2,2-dimethyl-cyclopropane-carboxylate

STEP A 2-trifluoromethyl-3-formyl-(1H)-indole 6.1 g of aluminum chloride and 20 ml of methylene chloride were mixed together at −65° C. under an inert atmosphere and a solution of 4.61 g of 2-trifluoromethyl-(1H)-indole (J. Org. Chem., 1974 Vol. 39, p. 1836), 1.4 ml of nitromethane and 20 ml of methylene chloride were added at −60° C. 3.3 ml of dichloromethyl ether in solution in 10 ml of methylene chloride were added to the suspension of the resulting mixture was stirred for 15 minutes at −65° C. The temperature was allowed to rise and at about −10° C., a strong evolution of hydrochloric acid was observed which ceased at about 0° C. The black solution obtained was stirred for 30 minutes at 25° C. and the reaction mixture was poured into water and extracted with methylene chloride. The organic phases were washed with an aqueous solution of sodium bicarbonate, then with water and concentrated to dryness under reduced pressure to obtain 4.6 g of 2-trifluoromethyl-3-formyl-(1H)-indole.

STEP B 2-trifluoromethyl-(1H)-indol-3-yl methanol 2 g of potassium borohydride were added in small fractions at +5° C. to a solution of 4.6 g of the product of Step A, 150 ml of tetrahydrofuran and 30 ml of water and the mixture was stirred for one hour. The mixture was allowed to return to ambient temperature and the tetrahydrofuran was eliminated under reduced pressure. The resulting mixture was diluted with ether, washed with water, dried and concentrated under reduced pressure. The residue was chromatographed over silica (eluent: hexaneethyl acetate 7-3) to obtain 3 g of 2-trifluoromethyl-(1H)-indol-3-yl methanol melting at 106° C.

STEP C

[2-trifluoromethyl-(1H)-indol-3-yl]-methyl 1R,cis 3-(2,2-dibromoethenyl)-2,2-dimethyl-cyclopropane-carboxylate 645 mg of (2-trifluoromethyl-(1H)-indol-3-yl)-methanol, 20 ml of methylene chloride and 0.3 ml of pyridine were mixed together at +5° C. under an inert atmosphere and 0.6 ml of 3-(2,2-dibromoethenyl)-2,2-dimethyl-cyclopropane-carboxylic acid chloride were added dropwise. The reaction mixture was diluted with methylene chloride and washed with a solution of sodium acid phosphate. The organic phase was dried and concentrated to dryness under reduced pressure. The residue was chromatographed over silica and eluted with a mixture of hexane and ethyl acetate (85/15) to obtain 1.45 g of [2-trifluoromethyl-(1H)-indol-3-yl]-methyl 1R cis 3-(2,2-dibromoethenyl)-2,2-dimethyl-cyclopropane-carboxylate with a specific rotation of $[\alpha]_D^{20} = -13°\pm2°$ (c=0.5% in CHCl$_3$).

Analysis: $C_{18}H_{16}Br_2F_3NO_2$ molecular weight;=495.148, Calculated: %C 43.66 %H 3.26 %N 2.83 %Br 32.28 %F 11.51, Found: 44.4, 3.4, 2.8, 32.0, 11.0.

EXAMPLE 2

[2-trifluoromethyl-1-(2-propynyl)-(1H)-indol-3-yl]-methyl 1R,cis 3-(2,2-dibromomethenyl)-2,2-dimethyl-cyclopropane-carboxylate

STEP A 1-(2-propynyl)-2-trifluoromethyl-(1H)-indole 8.57 g of 2-trifluoromethyl-1H-indole described in J. Org. Chem. (1983) 48-3233 and 10 ml of tetrahydrofuran were mixed together under an inert atmosphere at +5° C. and after 15 minutes, 2.4 g of sodium hydride in oil were added. After 2 minutes, 4.5 ml of 2-bromo-propyne were introduced and the resulting mixture was stirred for 30 minutes at +5° C., then for one hour at 25° C. Another 4.5 ml of bromo-propyne were added and the mixture was stirred for 4 hours and then poured into an iced solution of monosodium phosphate and extracted with ethyl ether. The extracts were concentrated to dryness by distillation under reduced pressure and the residue was chromatographed over silica and eluted with a mixture of hexane and ethyl acetate (95/5) to obtain 8.88 g of 1-(2-propynyl)-2-trifluoromethyl-(1H)-indole melting at 59° C.

STEP B 1-(2-propynyl)-2-trifluoromethyl-3-formyl-(1H)-indole

Using the procedure of Example 1, 8.8 g of 1-(2-propynyl)-2-trifluorometyl-(1H)-indole were reacted to obtain 6.70 g of 1-(2-propynyl)-2-trifluoromethyl-3-formyl-(1H)-indole melting at 106° C.

STEP C 1-(2-propynyl)-2-trifluoromethyl-(1H)-indol-3-yl methanol 5.54 g of 1-(2-propynyl)-2-trifluoromethyl-3-formyl-(1H)-indol, 120 ml of tetrahydrofuran and 20 ml of water were mixed together at +5° and 2 g of potassium borohydride were added in small fractions. The mixture was concentrated to a small volume by distillation under reduced pressure and ethyl ether was added. The organic phase was washed with salted water and concentrated to dryness by distillation under reduced pressure to obtain 5.6 g of 1-(2-propynyl)-2-trifluoromethyl-(1H)-indol-3-yl methanol melting at 90° C.

STEP D

[2-trifluoromethyl-1-(2-propynyl)-(1H)-indol-3-yl]-methyl 1R,cis 3-(2,2-dibromoethenyl)-2,2-dimethyl-cyclopropane-carboxylate 1 g of 1-(2-propynyl)-2-trifluoromethyl-(1H)-indol-3-yl-methanol, 10 ml of methylene chloride and a solution of 1.4 g of 3-(2,2-dibromoethenyl)-2,2-dimethyl-cyclopropane carboxylic acid in 10 ml of methylene chloride were mixed together under an inert atmosphere and 1.05 g of dicyclohexylcarbodiimide and 100 mg of 4-dimethylamino-pyridine in 8 ml of methylene chloride were introduced at 0° C. The mixture was stirred for 15 minutes at 0° C., then for one hour at 20° C. After filtering, the filtrate was concentrated to dryness by distillation under reduced pressure and isopropyl ether was added. After filtering and concentrating, the residue was chromatographed over silica and eluted with a mixture of hexane and isopropyl ether (9/1) to obtain 1.8 g of [2-trifluoromethyl-1-(2-propynyl)-(1H)-indol-3-yl]-methyl 1R, cis 3-(2,2-dibromoethenyl)-2,2-dimethyl-cyclopropane-carboxylate melting at 60° C. and having a specific rotation of $[\alpha]^{20} = -17° \pm 2°$ (c=0.5% in CHCl$_3$)

Analysis: $C_{21}H_{18}Br_2F_3NO_2$; molecular weight=533.196, Calculated: %C 47.31, %H 3.40, %Br 29.97, %F 10.69, %N 2.63, Found: 47.3, 3.4, 29.8, 10.9, 2.7.

EXAMPLE 3

[1-(2-propynyl)-2-trifluoromethyl-indol-3-yl]-methyl 1R, cis (E) 2,2-dimethyl-3-[2-fluoro-3-oxo-3-ethoxy-propenyl]-cyclopropane-carboxylate Using the procedures of Example 2, 1 g of alcohol and 1.1 g of corresponding acid were reacted to obtain 1.84 g of [1-(2-propynyl)-2-trifluoromethyl-indol-3-yl]-methyl 1R,cis (E) 2,2-dimethyl-3-[2-fluoro-3-oxo-3-ethoxy-propenyl]-cyclopropane-carboxylate with a specific rotation of $[\alpha]_D^{20} = +12° \pm 2°$ (c=0.5% in CHCl$_3$)

Analysis: $C_{24}H_{23}F_4NO_4$; molecular weight=465.445, Calculated: %C 61.93, %H 4.98, %N 3.01, %F 16.33, Found: 62.0, 5.0, 3.3, 16.3.

EXAMPLE 4

[2-trifluoromethyl-(1H)-indol-3-yl]-methyl 1R, cis (Z) 2,2-dimethyl-3-[3-oxo-3-tertbutoxy-propenyl]-cyclopropane-carboxylate Using the procedure of Example 2, 1 g of alcohol and 1.2 g of corresponding acid were reacted to obtain 0.84 g of [2-trifluoromethyl-(1H)-indol-3-yl]-methyl 1R, cis (Z) 2,2-dimethyl-3-[3-oxo-3-tertbutoxypropenyl]-cyclopropane-carboxylate with a specific rotation of $[\alpha]_D^{20} = +38° \pm 2°$ (c=0.5% in CHCl$_3$).

Analysis: $C_{23}H_{26}F_3NO_4$; molecular weight=437.463, Calculated: %C 63.15, %H 5.99, %N 3.20, %F 13.03, Found: 63.1, 6.1, 3.1, 13.3.

EXAMPLE 5

[2-trifluoromethyl-1-(2-propynyl)-indol-(1H)-3-yl]-methyl 1R,cis (Z) 2,2-dimethyl-3-[3-oxo-3-tertbutoxy-propenyl]-cyclopropane-carboxylate Using the procedure of Example 2, 1 g of alcohol and 1.15 g of corresponding acid were reacted to obtain 1.67 g of [2-trifluoromethyl-1-(2-propynyl)-indol-(1H)-3-yl]-methyl 1R, cis (Z) 2,2-dimethyl-3-[3-oxo-3-tertbutoxy-propenyl]-cyclopropane-carboxylate melting at 60° C. and having a specific rotation of $[\alpha]_D^{20} = +33.5° \pm 2°$ (c=0.5% in CHCl$_3$).

Analysis: $C_{26}H_{28}F_3NO_4$; molecular weight 475.513, Calculated %C 65.67, %H 5.94, %F 11.99, %N 2.95, Found: 65.9, 6.0, 11.9, 2.9.

EXAMPLE 6

[2-trifluoromethyl-1-(2-propynyl)-(1H)-indol-3-yl]-methyl 1R, cis (Z) 2,2-dimethyl-3-[3-oxo-3-methoxy-propenyl]-cyclopropane-carboxylate Using the procedure of Example 2, 1 g of alcohol and 0.870 g of corresponding acid were reacted to obtain 1.7 g of [2-trifluormethyl-1-(2-propynyl)-(1H)-indol-3-yl]-methyl 1R,cis (Z) 2,2-dimethyl-3-[3-oxo-3-methoxy-propenyl]-cyclopropane-carboxylate melting at 66° C. with a specific rotation of $[\alpha]_D^{20} = +28° \pm 1°$ (c=1% in CHCl$_3$), Analysis: $C_{23}H_{22}F_3NO_4$; molecular weight=433.431, Calculated: %C 63.74, %H 5.17, %N 3.23, %F 13.15, Found: 63.9, 5.1, 3.2, 13.0.

EXAMPLE 7

[1-(2-propynyl)-2-trifluoromethyl-(1H)-indol-3-yl]-methyl 1R, cis (E) 2,2-dimethyl-3-[2-fluoro-3-oxo-3-tertbutoxy-propenyl]-cyclopropane-carboxylate Using the procedure of Example 2, 1.48 g of alcohol and 1.54 g of corresponding acid were reacted to obtain 2.03 g of [1-(2-propynyl)-2-trifluoromethyl-(1H)-indol-3-yl]-methyl 1R,cis (E) 2,2-dimethyl-3-[2-fluoro-3-oxo-3-tertbutoxy-propenyl]-cyclopropane-carboxylate with a specific rotation of $[\alpha]_D^{20} = $ at $-10.5° +1°$ (c=1% in toluene).

Analysis: $C_{26}H_{27}F_4NO_4$; molecular weight =493.504 Calculated: %C 63.28, %H 5.51, %N 2.84, %F 15.40, Found: 63.5, 5.6, 2.7, 15.5.

EXAMPLE 8

[1-benzyl-2-trifluoromethyl-(1H)-indol-3-yl]-methyl 1R, cis 3-(2,2-dibromoethenyl)-2,2-dimethylcyclopropane-carboxylate Using the procedure of Example 1, 1.51 g of alcohol and 1.72 g of corresponding acid chloride were reacted to obtain 2.23 g of [1-benzyl-2-trifluoromethyl-(1H)-indol-3-yl]-methyl 1R,cis 3-(2,2-dibromoethenyl)-2,2-dimethylcyclopropane-carboxylate with a specific rotation of $[\alpha]_D^{20} = -19° \pm 1°$ (c=1% in CHCl$_3$).

Analysis: $C_{25}H_{22}Br_2F_3NO_2$; molecular weight=585.273, Calculated: %C 51.30, %H 3.79, %N 2.39, %Br 27.31, %F 9.74, Found: 51.0, 3.7, 2.4, 27.6, 9.4.

1-benzyl-2-trifluoromethyl-(1H)-indol-3-yl methanol used in Example 8 can be prepared as follows:

STEP A 1-benzyl-2-trifluoromethyl-(1H)-indole 8.6 g of 2-trifluoromethyl-(1H)-indole and 100 ml of tetrahydrofuran were mixed together under an inert atmosphere and cooled to 0° C. Over 15 minutes, about 2.4 g of a suspension of sodium hydride at 50% in oil was added in small fractions and 6.5 ml of benzyl bromide in solution in 10 ml of tetrahydrofuran were introduced over 5 minutes. The mixture was stirred for 42 hours at ambient temperature and then was poured into water saturated with monosodium phosphate. The mixture was extracted with ethyl ether, and the extracts were dried and concentrated to dryness by distillation under reduced pressure. The residue was chromatographed over silica and eluted with a mixture of hexane and ethyl acetate (9/1) to obtain 12.54 g of 1-benzyl-2-trifluoromethyl-(1H)-indole melting at approx. 20° C.

STEP B 1-benzyl-2-trifluoromethyl-3-formyl-(1H)-indole

Using the procedure of Step A for the preparation of the starting product of Example 1, 11.07 g of 1-benzyl-2-trifluoromethyl-(1H)-indole were reacted to obtain 7.94 g of 1-benzyl-2-trifluoromethyl-3-formyl-(1H)-indole.

STEP C 1-benzyl-2-trifluoromethyl-(1H)-indol-3-yl-methanol

Using the procedure of Step B for the preparation of the starting product of Example 1, 7.9 g of 1-benzyl-2-trifluoromethyl-3-formyl-(1H)-indole were reacted to obtain 7.45 g of 1-benzyl-2-trifluoromethyl-(1H)-indol-3-yl-methanol melting at 96° C.

EXAMPLE 9

[1-benzyl-2-trifluoromethyl-(1H)-indol-3-yl]-methyl 1R,cis (E) 2,2-dimethyl-3-[2-fluoro-3-oxo-3-tertbutoxy-propenyl]-cyclopropane-carboxylate Using the procedure of Example 2, 1.52 g of alcohol and 1.33 g of corresponding acid were reacted to obtain 1.90 g of [1-benzyl-2-trifluoromethyl-(1H)-indol-3-yl]-methyl 1R,cis (E) 2,2-dimethyl-3-[2-fluoro-3-oxo-3-tert-butoxy-propenyl]-cyclopropane-carboxylate with a specific rotation of $[\alpha]_D^{20} = +4° \pm 1°$ (c=0.5% in toluene).

Analysis: $C_{30}H_{31}F_4NO_4$; molecular weight=545.58, Calculated: %C 66.05, %H 5.73, %N 2.57, %F 13.93, Found: 66.2, 5.7, 2.6, 13.9.

EXAMPLE 10

(RS) α-cyano-[1-(2-propynyl)-2-trifluoromethyl-(1H)-indol-3-yl]-methyl 1R,cis 2,2-dimethyl-3-(2,2-bromoethenyl)-cyclopropane-carboxylate Using the procedure of Example 1, 0.65 g of cyanohydrin and 0.77 g of corresponding acid chloride were reacted to obtain 0.72 g of (RS) α-cyano-[1-(2-propynyl)-2-trifluoromethyl-(1H)-indol-3-yl]-methyl 1R,cis 2,2-dimethyl-3-(2,2-bromoethenyl)-cyclopropane-carboxylate with a specific rotation of $[\alpha]_D^{20} = +5° \pm 1°$ (c=1.4% in toleuene).

Analysis: $C_{22}H_{17}Br_2F_3N_2O_2$; molecular weight=558.205, Calculated: %C 47.34, %H 3.07, %N 5.02, %Br 28.63, %F 10.21, Found: 47.6, 3.1, 5.0, 29.1, 10.4.

EXAMPLE 11

(RS) α-cyano-[1-(2-propynyl)-2-trifluoromethyl-(1H)-indol-3-yl]-methyl 1R,cis (E) 2,2-dimethyl-3-[2-fluoro-3-oxo-3-tertbutoxy-propenyl]-cyclopropane-carboxylate Using the procedure of Example 2, 0.65 g of cyanohydrin and 0.6 g of corresponding acid were reacted to obtain 0.73 g of (RS) α-cyano [1-(2-propynyl)-2-trifluoromethyl)-(1H)-indol-3-yl]-methyl 1R,cis (E) 2,2-dimethyl-3-[2-fluoro-3-oxo-3-tertbutoxy-propenyl]-cyclopropane-carboxylate with a specific rotation of $[\alpha]_D^{20} = +25° \pm 1°$ (c=0.8% in toluene).

Analysis: $C_{27}H_{26}N_2F_4O_4$; molecular weight=518.519, Calculated: %C 62.54, %H 5.05, %N 5.40, %F 14.66, Found: 62.5, 4.9, 5.6, 14.8.

The alcohols used in Examples 10 and 11 were prepared according to the Netherlands Patent Application 65-17259 published on 1st July 1966.

EXAMPLE 12

[1-(2-propynyl)-2-trifluoromethyl-(1H)-indol-3-yl]-methyl 1R,cis (Z) 2,2-dimethyl-3-[1,1,1,3,3,3-hexafluoro-2-propyloxy)-3-oxo-1-propenyl]-cyclopropane-carboxylate 1.35 g of 1R,cis 2,2-dimethyl-3-[(Z) 3-oxo-3-[2-(1,1,1,3,3,3-hexafluoro)-propoxy]-1-propenyl]-cyclopropane-carboxylic acid prepared as in European Patent No. 0,048,186, 4 ml of a solution of dichloromethane containing 1 g of 1-(2-propynyl) [2-trifluoromethyl-(1H)-indol-3-yl]-methanol and 16 ml of dichloromethane were mixed together under an inert atmosphere, then cooled to −10° C. Over 5 minutes, 838 mg of dicyclohexylcarbodiimide and 46 mg of 4-dimethylaminopyridine in 10 ml of dichloromethane were added and stirring was maintained for one hour at −10° C./−5° C. After separating and concentrating to dryness under reduced pressure, the residue was chromatographed over silica (eluent: hexane-ethyl acetate 9-1) to obtain 1.58 g of [1-(2-propynyl)-2-trifluoromethyl-(1H)-indol-3-yl]-methyl 1R,cis (Z) 2,2-dimethyl-3-[1,1,1,3,3,3-hexafluoro-2-propyloxy)-3-oxo-1-propenyl]-cyclopropane-carboxylate (isomer delta Z)

melting at 92° C. and having a specific rotation of [α]$_D^{20}$=−13°±1.5° (c=0.7% in toluene).

Analysis: $C_{25}H_{30}F_9NO_4$; molecular weight=569.429, Calculated: %C 52.73, %H 3.54, %N 2.46, %F 30.03, Found: 52.9, 3.6, 2.5, 29.9.

EXAMPLE 13

[1-(2-propynyl)-2-trifluoromethyl-(1H)-indol-3-yl]-methyl 1R,cis (E) 2,2-dimethyl-3-[(1,1,1,3,3,3,-hexafluoro-2-propyloxy)-3-oxo-1-propenyl]-cyclopropane-carboxylate Using the procedure of Example 12, 1.1 g of the alcohol of Example 12 and 1.45 g of the acid of Example 12 were reacted but maintaining the reaction medium with stirring for one hour and a half at +5°/+10° C., then for one hour and a half at ambient temperature to obtain 1.58 g of [1-(2-propynyl)-2-trifluoromethyl-(1H)-indol-3-yl]-methyl 1R, cis (E) 2,2-dimethyl-3-[(1,1,1,3,3,3-hexafluoro-2-propyloxy)-3-oxo-1-propenyl]-cyclopropane-carboxylate (isomer delta Z) which was purified by chromatography over silica (eluent: hexane-isopropyl ether 7-3). The product melted at 92° C. and had a specific rotation of [α]$_D^{20}$=−49.5°±2° (c=0.6% in toluene).

Analysis: $C_{25}H_{20}F_9NO_4$; molecular weight=569.429, Calculated: %C 52.73, %H 3.54, %N 2.46, %F 30.03, Found: 52.8, 3.5, 2.5, 30.3.

EXAMPLE 14

1(RS) [1-(2-propynyl)-2-trifluoromethyl-(1H)-indol-3-yl]-ethyl 1R,cis (E) 2,2-dimethyl-3-[2-fluoro-3-(1,1-dimethylethoxy)-3-oxo-propenyl]-cyclopropane-carboxylate Using the procedure of Example 12, 1.06 g of 1(RS) [1(2-propynyl)-2-trifluoromethyl-(1H)-indol-3-yl]-methanol and 1.033 g of appropriate acid were reacted while maintaining the reaction medium with stirring at ambient temperature for 22 hours to obtain 1.41 g of 1(RS) [(1-(2-propynyl)-2-trifluoromethyl-(1H)-indol-3-yl]-ethyl 1R,cis (E) 2,2-dimethyl-3-[2-fluoro-3-(1,1-dimethylethoxy)-3-oxo-1-propenyl]-cyclopropane-carboxylate with a specific rotation of [α]$_D^{20}$=−1.6°±1.4° (c=0.6% in toluene).

Analysis: $C_{27}H_{29}F_4NO_4$; molecular weight=507.531, Calculated: %C 63.90, %H 5.76, %N 2.76, %F 14.96, Found: 64.0, 5.9, 2.9, 15.0.

1(RS) [1-(2-propynyl)-2-trifluoromethyl-(1H)-indol-3-yl]-ethanol used in Example 14 was prepared as follows:

3.55 g of 1-(2-propynyl)-2-trifluoromethyl-3-formyl-(1H)-indole in 30 ml of ether was cooled to −10° C. and over 20 minutes, 10 ml of a solution of magnesium methyl iodide in ether (1.6M) were added with stirring for one hour at −10°/−5° C. After allowing the mixture to return to ambient temperature and stirring for 30 minutes, once again 2 ml of the magnesium solution were added. The mixture was stirred for 45 minutes and then poured into an aqueous solution of iced ammonium chloride. After extraction with ether, the extracts were dried and the solvent was eliminated under reduced pressure. The residue was chromatographed over silica (eluent: hexane-ethyl acetate 8-2) to obtain 3.0 g of 1(RS) [1-(2-propynyl)-2-trifluoromethyl-(1H)-indol-3-yl]-ethyl 1R,cis (E) 2,2-dimethyl-3-[2-fluoro-3-(1,1-dimethylethoxy-3-oxo-1-propenyl]-cyclopropane-carboxylate.

EXAMPLE 15

1(RS) [1-(2-propynyl)-2-trifluoromethyl-(1H)-indol-3-yl]-ethyl 1R, cis (E) 2,2-dimethyl-3-(3-ethoxy-2-fluoro-3-oxo-1-propenyl)-cyclopropane-carboxylate Using the procedure of Example 12, 1.08 g of 1(RS) [1-(2-propynyl)-2-trifluoromethyl-(1H)-indol-3-yl]-ethanol and 4 ml of chloromethylene solution of the appropriate acid (M) were reacted with stirring of the reaction medium at ambient temperature for 2 hours and a half to obtain 1.47 g of 1(RS) [1-(2-propynyl)-2-trifluoromethyl-(1H)-indol-3-yl]-ethyl 1R,cis (E) 2,2-dimethyl-3-(3-ethoxy-2-fluoro-3-oxo-1-propenyl)-cyclopropane-carboxylate with a specific rotation of [α]$_D^{20}$=+16°±1.4° (c=0.7% in toluene).

Analysis: $C_{25}H_{25}F_4NO_4$, Calculated: %C 62.63, %H 5.26, %N 2.92, %F 15.85, Found: 62.9, 5.1, 2.8, 15.8.

EXAMPLE 16

1(RS) [1-(2-propynyl)-2-trifluoromethyl-(1H)-indol-3-yl]-ethyl 1R,cis 2,2-dimethyl[-3-(2,2-dibromoethenyl)-cyclopropane-carboxylate 0.82 g of 1 (RS) [1-(2-propynyl)-2-trifluoromethyl-(1H)-indol-3-yl]-ethanol and 20 ml of 3-(2,2-dibromoethenyl)-2,2-dimethyl-cyclopropane-carboxylic acid chloride were mixed together at ambient temperature under an inert atmosphere, and 0.3 ml of pyridine were added. After stirring for 18 hours, the solvents were evaporated under reduced pressure to obtain 3.15 g of crude product which was purified by chromatography over silica (eluent: hexane-ethyl acetate 9-1 then hexane-isopropyl ether 9-1) to obtain 1(RS) [1-(2-propynyl)-2-trifluoromethyl-)1H)-indol-3-yl]-ethyl 1R,cis 2,2-dimethyl [3-(2,2-dibromoethenyl)-cyclopropane-carboxylate with a specific rotation of [α]$_D^{20}$=−30.5°±1.6° (c=0.6% in toluene).

Analysis: $C_{22}H_{20}Br_2F_3NO_2$, Calculated: %C 48.29, %H 3.68, %N 2.56, %F 10.42, %Br 29.2, Found: 48.3, 3.6, 2.6, 10.7, 28.5.

EXAMPLE 17

1(RS) [1-(2-propynyl)-2-trifluoromethyl-(1H)-indol-3-yl]-prop-2-ynyl 1R,cis (E) 2,2-dimethyl-3-(3-ethoxy-2-fluoro-3-oxo-1-propenyl)-cyclopropane-carboxylate Using the procedure of Example 12, 0.95 g of 1(RS) [1-(2-propynyl)-2-trifluoromethyl-(1H)-indol-3-yl]-prop-2-ynyl alcohol and 0.76 g of appropriate acid were reacted with stirring of the reaction medium at ambient temperature for 19 hours to obtain 1.21 g of 1(RS) [1-(2-propynyl)-2-trifluoromethyl-(1H)-indol-3-yl]-prop-2-ynyl 1R,cis (E) 2,2-dimethyl-3-(3-ethoxy-2-fluoro-3-oxo-1-propenyl)-cyclopropane-carboxylate with a specific rotation of [α]$_D^{20}$=−8.5°±1° (c=1% in toluene).

Analysis: $C_{26}H_{23}F_4NO_4$; molecular weight=489.472, Calculated: %C 63.80, %H 4.74, %N 2.86, %F 15.52, Found: 64.1, 4.9, 3.0, 15.4.

1(RS) [1-(2-propynyl)-2-trifluoromethyl-(1H)-indol-3-yl]-prop-2-ynyl alcohol used in Example 17 was prepared as follows:

4.5 g of 1-(2-propynyl)-2-trifluoromethyl-3-formyl-(1H)-indole in 30 ml of tetrahydrofuran were cooled at −15° C. and over 15 minutes, 26 ml of a solution of magnesium ethynyl bromide in tetrahydrofuran (0.8M) were added. After stirring for one hour at −5° C., another 5 ml of magnesium solution were added, and the mixture was allowed to return to ambient temperature. After stirring for 30 minutes and then pouring into a saturated aqueous solution of monosodium phosphate, extraction was carried out with isopropyl ether. The solvent was eliminated under reduced pressure to obtain 5.89 g of crude product which was purified by chromatography over silica (eluent: hexane-ethyl acetate 9-1) to obtain 1.91 g of 1(RS) [1-(2-propynyl)-2-trifluoromethyl-(1H)-indol-3-yl]-prop-2-ynyl alcohol melting at 98° C.

EXAMPLE 18

1(RS) [1-(2-propynyl)-2-trifluoromethyl-(1H)-indol-3-yl]-prop-2-ynyl 1R,cis (E) 2,2-dimethyl-3-[3-(1,1-dimethylethoxy)-2-fluoro-3-oxo-1-propenyl]-cyclopropane-carboxylate Using the procedure of Example 12, 0.95 g of the alcohol of Example 17 and 0.9 g of appropriate acid were reacted with stirring of reaction medium at ambient temprature for 18 hours to obtain 1.19 g of 1(RS) [1-(2-propynyl)-2-trifluoromethyl-(1H)-indol-3-yl]-prop-2-ynyl 1R,cis (E) 2,2-dimethyl-3-[3-(1,1-dimethylethoxy)-2-fluoro-3-oxo-1-propenyl]cyclopropane-carboxylate with a specific rotation of $[\alpha]_D^{20} = +11.5° \pm 1°$ (c=1% in toluene).

Analysis: $C_{28}H_{27}F_4NO_4$; molecular weight=517.526, Calculated: %C 65.00, %H 5.26, %N 2.70, %F 14.68, Found: 65.1, 5.3, 2.7, 14.9.

EXAMPLE 19

Acaricide compositon in concentrated soluble form

A homogeneous mixture of 50 g of the product of Example 5, 100 g of Piperonyl butoxide, 50 g of Tween 70, 50 g of Topanol A and sufficient Water for 1000 g was prepared.

EXAMPLE 20

Acaricide compositions in emulsifiable concentrated form

A homogeneous mixture of 100 g of the Product of Example 12, 64 g of Atlox 4851, 32 g of Atlox 4855 and sufficient xylene for 1000 g was prepared.

EXAMPLE 21

Acaricide compositions in the form of wettable powder

A homogeneous mixture of 50 g of the Product of Example 12, 2 g of Butyl hydroxy toluene, 60 g of Glycol, 80 g of Polyethoxy ether of fatty alcohols, 60 g of Sodium naphthalene sulfonate and sufficient Kaolin for 1000 g were prepared.

EXAMPLE 22

Fumigant insecticide compositions

A homogeneous mixture of 10 g of the Product of Example 7, 250 g of Tabu powder, 390 g of Cedar leaf powder, 340 g of Pine wood dust, 5 g of Brilliant green and 5 g of p-nitrophenol was prepared.

Study of acaricide activity on Tetranychus Urticae

Test of killing adult insects.

Bean plant leaves infested with 50 mites per leaf and coated with birdlime on their edges were used. 2.5 ml of aqueous solution of compound was sprayed per leaf, using decreasing concentrations to determine the $LC_{50}$ of the compounds of the invention. The experimental results are summarized in the following Table.

| Product of example | $LC_{50}$ product (mg/l) |
|---|---|
| 5 | 283 |
| 7 | 132 |
| 12 | 23 |

Study of the insecticide and activity on Alphis Cracivora

Bean plants were used which were divided into two groups. (a) The first group of plants were treated with the compound of the invention spraying 1 ml of solution containing decreasing quantities of compound of the invention per liter on each leaf. Each leaf was infested with twenty aphides and surrounded by gauze to prevent the aphides from leaving. The $LD_{50}$ of the compound of the invention was determined. (b) The second group of plants or control group was not treated and each leaf was infested directly with twenty aphides. The experimental results are summarized in the following Table.

| Product of example | $LD_{50}$ Product of invention (mg/l) |
|---|---|
| 2 | 6.8 |
| 3 | 5.7 |
| 5 | 5.7 |
| 7 | 3.4 |
| 12 | 1.5 |

Various modifications of the compounds and methods of the invention may be made without departing from the spirit or scope thereof and it should be understood that the invention is intended to be limited only as defined in the appended claims.

What is claimed is:

1. A compound of the formula

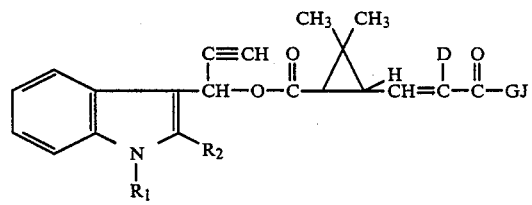

wherein $R_1$ is selected from the group consisting of hydrogen, alkyl of 1 to 8 carbon atoms and aralkyl of 7 to 18 carbon atoms, $R_2$ is selected from the group consisting of hydrogen, alkyl of 1 to 8 carbon atoms and —$CF_3$, D is alkoxy of 1 to 8 carbon atoms, G is —O— or —S— and J is selected from the group consisting of alkyl and halogenated alkyl of 1 to 8 carbon atoms, alkenyl and alkynyl of 2 to 8 carbon atoms and cycloalkyl of 3 to 8 carbon atoms.

2. A compound of claim 1 wherein $R_1$ is benzyl.

3. A compound of claim 1 wherein $R_1$ is hydrogen.

4. A compound of claim 1 wherein $R_2$ is —$CF_3$.

5. A compound of claim 1 which is [1-(2-propynyl)-2-trifluoromethyl-(1H)-indol-3-yl]-methyl 1R,cis (ΔZ)-2,2-dimethyl-3-[1,1,1,3,3,3-hexafluoro-2-propyloxy)-3-oxo-1-propenyl]-cyclopropane-carboxylate.

6. An insecticidal composition comprising an insecticidally effective amount of at least one compound of claim 1 and a carrier.

7. A composition of claim 6 wherein $R_1$ is benzyl.

8. A composition of claim 6 wherein $R_1$ is hydrogen.

9. A composition of claim 6 wherein $R_2$ is —$CF_3$.

10. A composition of claim 6 wherein the active compound is [1-(2-propynyl)-2-trifluoromethyl-(1H)-indol-3-yl]-methyl 1R, cis (ΔZ)-2,2-dimethyl-3-[(1,1,1,3,3,3-hexafluoro-2-propyloxy)-3-oxo-1-propenyl]-cyclopropane-carboxylate.

11. A method of combatting insects comprising contacting insects with an insecticidally effective amunt of at least one compound of claim 1.

12. A method of claim 11 wherein $R_1$ is benzyl.

13. A method of claim 11 wherein $R_1$ is hydrogen.

14. A method of claim 11 wherein $R_3$ is —$CF_3$.

15. A method of claim 11 wherein the active compound is [1-(2-propynyl)-2-trifluoromethyl-(1H)-indol-3-yl]-methyl 1R,cis (ΔZ)-2,2-dimethyl-3-[(1,1,1,3,3,3-hexafluoro-2-propyloxy)-3-oxo-1-propenyl]-cyclopropane-carboxylate.

16. A method of combatting acarids comprising contacting acaride with an acaricidally effective amount of at least one compound of claim 1.

17. A method of combatting nematodes comprising contacting nematodes with a nematocidally effective amount of at least one compound of claim 1.

* * * * *